United States Patent [19] [11] 4,002,680
Brunetti et al. [45] Jan. 11, 1977

[54] PROCESS FOR THE MANUFACTURE OF ACYLHYDRAZINES

[75] Inventors: Heimo Brunetti; Andreas Schmidt, both of Reinach; Siegfried Rosenberger, Riehen, all of Switzerland

[73] Assignee: Ciba-Geigy Corporation, Ardsley, N.Y.

[22] Filed: May 17, 1973

[21] Appl. No.: 361,352

[30] Foreign Application Priority Data

May 31, 1972 Switzerland .................. 8031/72

[52] U.S. Cl. ............... 260/559 H; 260/249.6; 260/249.8; 260/249.9; 260/404.5; 260/557 H; 260/558 H; 260/561 H

[51] Int. Cl.² .................. C07C 103/20

[58] Field of Search ........ 260/404.5, 557 H, 404.5, 260/558 H, 559 H, 561 H, 249.6, 249.8, 249.9

[56] References Cited

UNITED STATES PATENTS

| | | | |
|---|---|---|---|
| 2,418,336 | 4/1947 | D'Alelio et al. | 260/249.5 |
| 2,615,862 | 10/1952 | McFarlane et al. | 260/558 H |
| 2,838,520 | 6/1958 | Mueller et al. | 260/559 H X |
| 2,874,189 | 2/1959 | Micucci et al. | 260/559 H X |
| 2,944,071 | 7/1960 | Pessolano et al. | 260/404.5 |
| 2,970,159 | 1/1961 | Gutmann et al. | 260/404.5 |
| 3,379,754 | 4/1968 | Bernstein et al. | 260/558 H |
| 3,441,606 | 4/1969 | Moore et al. | 260/558 H X |
| 3,641,045 | 2/1972 | Meek | 260/307 G |
| 3,660,438 | 5/1972 | Dexter | 260/404.5 |
| 3,849,492 | 11/1974 | Brunetti et al. | 260/559 H |
| 3,850,918 | 11/1974 | D'Alelio et al. | 260/249.9 |
| 3,884,874 | 5/1975 | Rosenberger et al. | 260/559 H X |

OTHER PUBLICATIONS

Caglioti et al., Journ. Org. Chem., vol. 33, No. 7, July 1968.

Primary Examiner—Ethel G. Love
Attorney, Agent, or Firm—Charles W. Vanecek

[57] ABSTRACT

1,2-Diacylhydrazines are prepared by a new process by reacting acylhydrazides and carbonic acids in the presence of an inorganic acid chloride.

13 Claims, No Drawings

PROCESS FOR THE MANUFACTURE OF ACYLHYDRAZINES

The present invention relates to a process for the manufacture of 1,2-diacylhydrazines of the formula I $$R_1-CO-NHNH-R_2 \quad (I)$$

wherein $R_1$ denotes an aliphatic, cycloaliphatic, araliphatic, aromatic or heterocyclic radical, $R_2$ denotes a radical of the formula $R_3$—CO— or —X—NH—NH—CO—$R_1$, $R_3$ denotes an aliphatic, cycloaliphatic, araliphatic, aromatic or heterocyclic radical and X denotes the diacyl radical of a divalent aliphatic, araliphatic, aromatic or heterocyclic dicarboxylic acid, or an unsubstituted or substituted 2,4,6-triazinyl radical, characterised in that one equivalent of a monoacylhydrazide of the formula II $$R_1-CO-NH-NH_2 \quad (II)$$

and about one equivalent of a monocarboxylic acid of the formula III $$R_3-COOH \quad (III)$$

is reacted with approximately one equivalent of an inorganic acid chloride, or one equivalent of a dihydrazide of the formula IV $$H_2N-NH-X-NH-NH_2 \quad (IV)$$

and two equivalents of a monocarboxylic acid of the formula V $$R_1-COOH \quad (V)$$

or two equivalents of a monoacylhydrazide of the formula II and approximately one equivalent of a compound of the formula VI $$HO-Y-OH \quad (VI)$$

wherein Y denotes the diacyl radical of a divalent aliphatic, araliphatic, aromatic or heterocyclic dicarboxylic acid, are reacted with approximately two equivalents of an inorganic acid chloride.

The new process can optionally be carried out in an inert solvent and optionally in the presence of a catalyst.

It is known that diacylated hydrazines can be manufactured in good yields from carboxylic acid hydrazides and carboxylic acid chlorides. This method of manufacture presupposes the separate manufacture of the carboxylic acid chloride, which is frequently unstable, sensitive to moisture and does not store well.

In contrast, the process according to the invention permits the manufacture of diacylated hydrazines in a single process stage from stable and easily accessible starting materials.

A further advantage of the process according to the invention is that it is not necessary to remove, by distillation, any possible excess of inorganic acid chloride, such as thionyl chloride or phosphorus trichloride and the like. The desired product precipitates directly, as the most sparingly soluble component, from the mixture. Since the reaction can be carried out at elevated temperature, the gaseous decomposition products, particularly hydrochloric acid, easily escape from the reaction mixture.

The process according to the invention is preferentially used to manufacture the compounds disclosed in the following Offenlegungsschriften:

a. The compounds of the formula Ia of DOS 2,124,641

$$R-\overset{O}{\underset{\|}{C}}-NH-NH-\overset{O}{\underset{\|}{C}}\left[X'-\overset{O}{\underset{\|}{C}}\right]_n NH-NH-\overset{O}{\underset{\|}{C}}-R \quad (Ia)$$

in which R denotes alkyl with 1 to 17 carbon atoms, cyclohexyl, or aralkyl optionally substituted by one or two alkyl groups each with 1 to 4 carbon atoms, and/or by a hydroxyl group; Phenol, chlorophenyl, dichlorophenyl, and phenyl optionally substituted by one or two alkyl groups with 1 to 4 carbon atoms and/or by a hydroxyl group in the m- or p-position; alkylphenyl with 7 to 14 carbon atoms, alkoxyphenyl with 7 to 24 carbon atoms or naphthyl, X' denotes the direct bond, an alkylene radical with 2 to 8 carbon atoms, a phenylene radical or a naphthylene radical and n denotes 0 or 1, such as, for example, N,N'-dibenzyloxalic acid dihydrazide or N,N'-diacetyladipic acid dihydrazide.

b. The compounds of the general formula Ib of DOS 2,129,996 in which $R_1'$ denotes hydrogen, alkyl with 1 to 18 carbon atoms, alkoxy with 1 to 18 carbon atoms, unsubstituted phenyl, phenyl substituted by lower alkyl groups, lower alkoxy groups, halogen and/or hydroxyl groups, the group or the group

wherein R₂' and R₃' independently of one another denote hydrogen, alkyl with 1 to 18 carbon atoms, cyclohexyl, benzyl, unsubstituted phenyl or phenyl substituted by one or two alkyl groups each with 1 to 8 carbon atoms, or R₂' and R₃' conjointly, with inclusion of the nitrogen atom, denote a saturated 5-membered to 7-membered heterocyclic ring and the rings A are unsubstituted or are substituted by 1 to 2 alkyl groups each with 1 to 18 carbon atoms, an alkoxy group with 1 to 18 carbon atoms and/or 1 to 3 chlorine atoms.

c. The compounds of the formula Ic of DOS 2,140,350

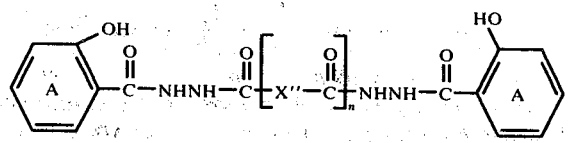

in which X'' denotes the direct bond, an alkylene radical with 1 to 8 carbon atoms, a phenylene radical or a naphthylene radical and n denotes 0 or 1, and the rings A are unsubstituted or one ring A or both rings A are substituted by alkyl groups, alkenyl groups, cycloalkyl groups, aralkyl groups, further hydroxyl groups, alkoxy groups, acyloxy groups, acylamino groups or halogen.

d. The compounds of the formula Id of DOS 2,150,131

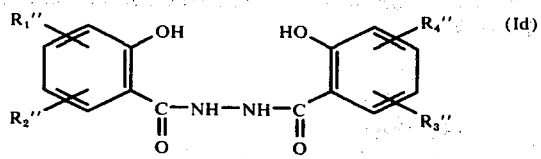

in which R₁'', R₂'', R₃'' and R₄'' independently of one another denote hydrogen, alkyl with 1 to 18 carbon atoms, alkenyl with 3 to 4 carbon atoms, cycloalkyl with 6 to 8 carbon atoms, aralkyl with 7 to 9 carbon atoms, alkoxy with 1 to 18 carbon atoms, phenyl or chlorine and R₁'' and R₃'' independently of one another also denote hydroxyl, acyloxy with 2–18 carbon atoms or acylamino with 2 – 18 carbon atoms.

e. The compounds of the formula Ie of DOS 2,231,307

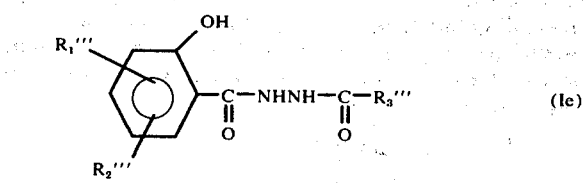

in which R₁''' denotes hydrogen, alkyl with 1 to 8 carbon atoms, alkenyl with 3 or 4 carbon atoms, cycloalkyl with 6 to 8 carbon atoms, aralkyl with 7 to 9 carbon atoms, phenyl, chlorine, hydroxyl, alkoxy with 1 to 18 carbon atoms, acyloxy with 2 to 18 carbon atoms or acylamino with 2 to 18 carbon atoms, R₂''' denotes hydrogen, alkyl with 1 to 5 carbon atoms, alkenyl with 3 or 4 carbon atoms, cyclohexyl, aralkyl with 7 to 9 carbon atoms or chlorine, R₃''' denotes alkyl with 2 to 21 carbon atoms, and cyclohexyl or the radical

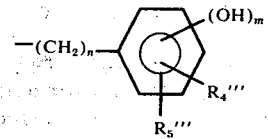

m denotes 0 or 1, n denotes 0 to 2 and, if the OH group is in the o-position to the —(CH₂)ₙ—group, the difference n-m is not less than 0, R₄''' denotes hydrogen, alkyl with 1 to 8 carbon atoms, alkenyl with 3 or 4 carbon atoms, cycloalkyl with 6 to 8 carbon atoms, aralkyl with 7 to 9 carbon atoms, phenyl, chlorine, hydroxyl, alkoxy with 1 to 18 carbon atoms, acyloxy with 2 to 18 carbon atoms or acylamino with 2 to 18 carbon atoms and R₅''', if m is 1, denotes hydrogen, alkyl with 1 to 5 carbon atoms, alkenyl with 3 or 4 carbon atoms, cyclohexyl, aralkyl with 7 to 9 carbon atoms, chlorine or hydroxyl or R₅''', if m is 0, denotes hydrogen, alkyl with 1 to 8 carbon atoms, alkenyl with 3 or 4 carbon atoms, cycloalkyl with 6 to 8 carbon atoms, aralkyl with 7 to 9 carbon atoms, phenyl, chlorine, hydroxyl, alkoxy with 1 to 18 carbon atoms, acyloxy with 2 to 18 carbon atoms or acylamino with 2 to 18 carbon atoms.

f. The compounds of the formula If disclosed in DOS 2,257,462

in which R₁ᴵⱽ and R₂ᴵⱽ independently of one another denote the unsubstituted phenyl group, a phenyl group substituted by a hydroxyl group in the m- or p-position, by one or two alkyl groups each with 1 to 4 carbon atoms, by one or two alkenyl groups each with 3 or 4 carbon atoms, by one or two cycloalkyl groups each with 6 to 8 carbon atoms, by one or two chlorine atoms, by one or two alkoxy groups each with 1 to 8 carbon atoms, by one or two acyloxy groups each with 2 to 18 carbon atoms, by an acylamino group with 2 to 18 carbon atoms or by an amino group in the o-position, or denote a pyridyl radical, or in which, if R₁ᴵⱽ denotes a substituted phenyl group, R₂ᴵⱽ also denotes hydrogen, alkyl with 1 to 18 carbon atoms, cyclohexyl or benzyl.

According to the invention, it is possible, for example, particularly readily to manufacture compounds of the formula I in which R₁ denotes a substituted aryl or aryl substituted by hydroxyl, for example aryl with 6 to 10 carbon atoms, such as phenyl, or unsubstituted aralkyl or aralkyl substituted by hydroxyl and/or lower alkyl, for example alkyl with 1 to 5 carbon atoms such as tert.butyl, for example aralkyl with 7 to 11 carbon atoms, or alkyl, for example alkyl with 1 to 20 carbon atoms, R₂ denotes a radical of the formula R₃—CO—or —X—NHNH—CO—R$_1$, R$_3$ denotes unsubstituted aryl or aryl substituted by hydroxyl and/or alkoxy, such as alkoxy with 1 to 10 carbon atoms, for example aryl with 6 to 10 carbon atoms such as phenyl, or alkyl such as, for example, alkyl with 1 to 20 carbon atoms, and X and Y denote a diacyl radical of a divalent alkanoic acid such as of an alkanoic acid with 2 to 10 carbon atoms.

According to the invention it is also possible to manufacture for example, N,N'-bis-(4-hydroxy-3,5-di-tert.-butyl-phenylpropionyl)hydrazine.

The process according to the invention can be carried out by first taking an acid hydrazide of the formulae II or IV, an acid of the formulae III, V or VI and, if the reaction is carried out in the presence of a catalyst, also the catalyst, in a solvent, and adding the inorganic acid chloride dropwise.

Examples of inorganic acid chlorides used are SOCl$_2$, PCl$_3$, POCl$_3$ and PCl$_5$.

Possible solvents are: aromatic hydrocarbons such as benzene, toluene or xylene, substituted aromatic compounds such as chlorobenzene, higher-boiling ethers such as ethylene glycon dimethyl ether, aliphatic hydrocarbons such as ligroin, and liquid amides such as dimethylformamide or dimethylacetamide.

Dimethylformamide or pyridine can be used as catalysts. The acid chlorides are preferably used in an excess of 10 to 50% calculated relative to the amount which would be necessary to form the acid chlorides of the acids III, V or VI.

The catalyst which is optionally present in the process according to the invention is employed, for example, in 1 to 50, preferably 20 to 40, mol per cent relative to the compounds of the formula II.

The process according to the invention is carried out, for example, at a temperature of 50° to 180° C, preferably at 120° to 150° C.

The compounds obtained according to the process of the invention are stabilisers for homopolymeric or copolymeric polyolefines against thermo-oxidative degradation, especially in the presence of transition metals.

The invention is described in more detail in the examples which follow.

EXAMPLE 1

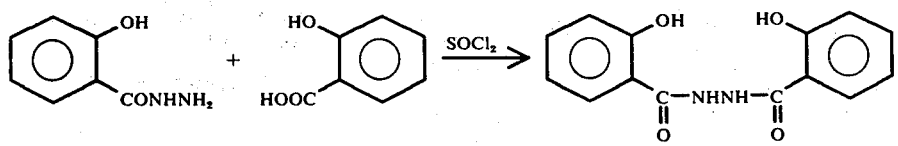

15.2 g (0.1 mol) of salicylic acid hydrazide and 13.8 g (0.1 mol) of salicylic acid are initially introduced into 200 ml of chlorobenzene and the mixture is heated to the boil (132° C). After adding 2.0 g (0.025 mol) of pyridine, 13.1 g (0.11 mol) of thionyl chloride are added dropwise over the course of 1 hour. The suspension which forms remains stirrable throughout. After cooling to room temperature, the solid material is filtered off, washed first with 20 ml of cold toluene and then with 20 ml of cold methanol, and dried in vacuo at 60° C. N,N'-Bis-salicyloylhydrazine, which has a melting point of 318°–320° C, is thus obtained in a yield of 73%.

If, in this example, the thionyl chloride is replaced by an equimolecular amount of phosphorous trichloride, N,N'-bis-salicyloyl-hydrazine is produced in 63% yield.

The catalyst can be replaced by dimethylformamide, or omitted entirely, without reducing the yield.

EXAMPLE 2

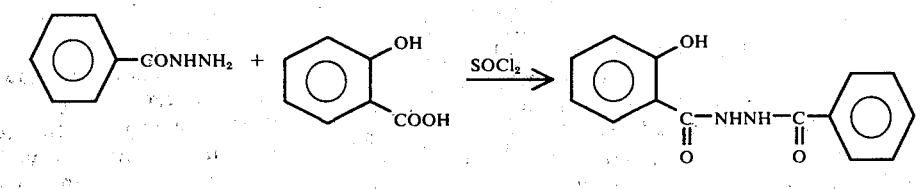

13.6 g (0.1 mol) of benzhydrazide and 13.8 g (0.1 mol) of salicylic acid are initially introduced into 200 ml of chlorobenzene and the mixture is heated to the boil. After adding 3.0 g (0.038 mol) of pyridine, 13.1 g (0.11 mol) of thionyl chloride are added dropwise over the course of 1 hour. The reaction starts immediately whilst the product separates out as a white precipitate. After cooling, the mixture is filtered and the product is washed with methanol and dried. N-Salicyloyl-N'-phenyl-hydrazine of melting point 259° C is thus obtained in 67% yield.

If, in this example, the benzhydrazide is replaced by 0.05 mol of adipic acid dihydrazide and otherwise the same procedure is followed, N,N'-bis-salicyloyl-adipic acid dihydrazide of melting point 252° C is obtained in 63% yield.

EXAMPLE 3

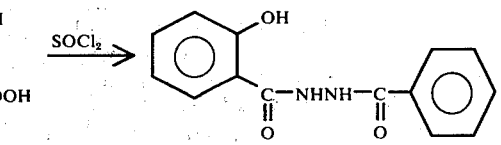

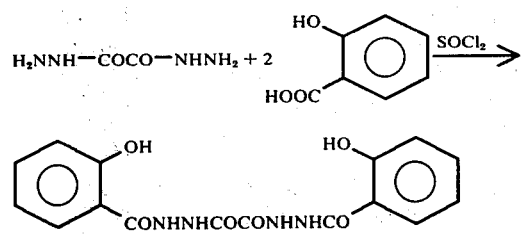

11.8 g (0.1 mol) of very finely powdered oxalic acid dihydrazide and 27.6 g (0.2 mol) of salicylic acid are suspended in 200 ml of dimethylacetamide and 26.2 g (0.22 mol) if thionyl chloride are added at 50°–70° C. The yellowish reaction mixture is stirred for a further hour at 70° C and then poured into 1 liter of water, whereupon a white solid precipitates. After isolation, and drying at 130° C in vacuo, N,N'-bis-salicyloyloxalic acid dihydrazide, which up to 320° C does not melt, is obtained. Yield: 69%.

EXAMPLE 4

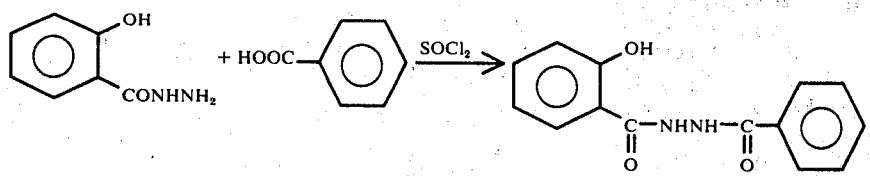

15.2 g (0.1 mol) of salicylic acid hydrazide and 12.2 g (0.1 mol) of benzoic acid are suspended in 200 ml of chlorobenzene, 3.0 g (0.038 mol) of pyridine are added and the mixture is heated to 130° C. 13.1 g (0.11 mol) of thionyl chloride are added dropwise at this temperature. The product immediately separates as a white precipitate. After stirring for 1 hour at 130° C, the mixture is cooled and filtered and the product is washed with petroleum ether. N-Salicyloyl-N'-phenyl-hydrazine of melting point 260° C is thus obtained in 62% yield.

EXAMPLE 5

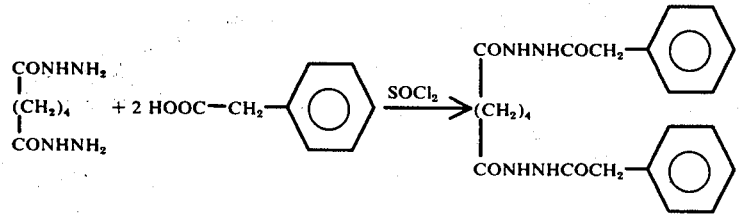

17.4 g (0.1 mol) of adipic acid dihydrazide and 27.2 g (0.2 mol) of phenylacetic acid are suspended in 230 ml of chlorobenzene, 2.0 g (0.025 mol) of pyridine are added and the mixture is heated to the boil. Thereafter 26.2 g (0.22 mol) of thionyl chloride are added dropwise, whereupon the vigorous reaction commences. The suspension turns slightly brown. After boiling for 1 hour it is cooled and filtered and the product is washed with methanol. N,N'-Diphenylacetyl-adipic acid dihydrazide of melting point 310°–312° C is thus obtained in 63% yield.

EXAMPLE 6

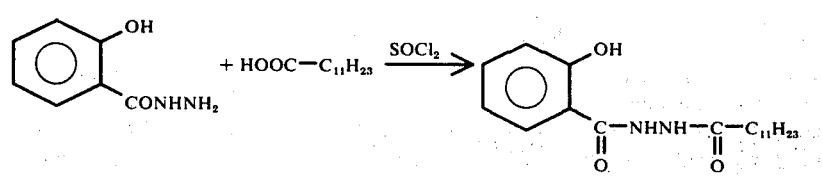

15.2 g (0.1 mol) of salicylic acid hydrazide and 20.0 g (0.1 mol) of lauric acid are suspended in 200 ml of chlorobenzene, 2.0 g (0.025 mol) of pyridine are added and the mixture is heated to the boil. 13.1 g (0.11 mol) of thionyl chloride are added dropwise at this temperature. The product separates out initially as a turbidity and then as a flocculent precipitate. After boiling for 1 hour the mixture is cooled and the product is filtered off and washed with a little benzene and then with petroleum ether. N-Salicyloyl-N'-lauroyl-hydrazine of melting point 158° C is thus obtained in a yield of 53%. The product can be recrystallised from ethylene glycol monomethyl ether.

EXAMPLE 7

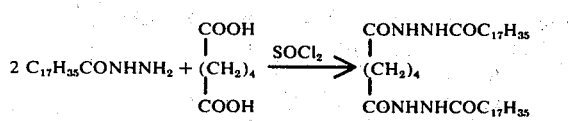

29.8 g (0.1 mol) of stearic acid hydrazide and 7.3 g (0.05 mol) of adipic acid in 300 ml of dimethylacetamide are warmed to 50° C. 13.1 g (0.11 mol) of thionyl chloride are added dropwise to this solution over the course of 10 minutes. The mixture is kept at 60° C for a further 2 hours and is then cooled and poured into a large excess of water. The product is obtained as a white precipitate. After filtration and drying, 73% of N,N'-di-stearoyl-adipic acid dihydrazide of melting point 244° C are obtained.

EXAMPLE 8

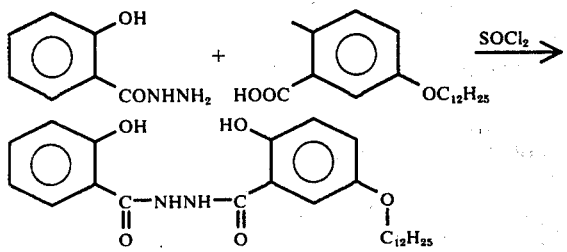

16.2 g (0.05 mol) of 2-hydroxy-5-dodecyloxy-benzoic acid and 7.6 g (0.05 mol) of salicyloylhydrazine are initially introduced into 100 ml of toluene, 5 ml of pyridine are added and the mixture is heated to 100° C whilst stirring well. 6.5 g (0.055 mol) of thionyl chloride dissolved in 20 ml of toluene are slowly added dropwise at this temperature. After the dropwise addition the mixture is stirred for a further 30 minutes at 100° C and is subsequently cooled to room temperature, and the product is filtered off, It is washed with toluene and then with alcohol, and thereafter dried in vacuo at 60° C. 14 g (61%) of N-salicyloyl-N'-(5-dodecyloxy-2-hydroxybenzoyl)-hydrazine of melting point 244° C are thus obtained.

EXAMPLE 9

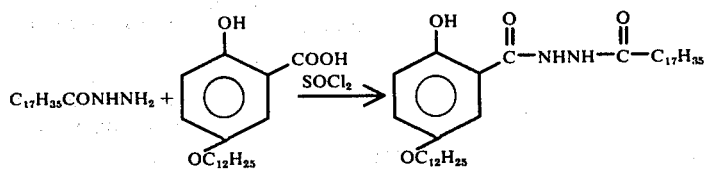

6.5 g (0.02 mol) of 2-hydroxy-5-dodecyloxy-benzoic acid and 6 g (0.02 mol) of stearoylhydrazine are initially introduced into 50 ml of dimethylacetamide and 2.7 g (0.022 mol) of thionyl chloride are added dropwise over the course of 20 minutes whilst stirring at 60° C. The mixture is stirred for a further 40 minutes at this temperature and subsequently cooled to 0° C and the product is filtered off and thoroughly washed with methanol. After recrystallisation from isopropanol, 7.5 g (62%) of N-stearoyl-N'-(5-dodecyloxy-2-hydroxybenzoyl)-hydrazine of melting point 143° C are obtained.

EXAMPLE 10

29.3 g (0.1 mol) of 3-(3,5-di-t.butyl-4-hydroxyphenyl)-propionic acid hydrazide and 7.3 g (0.05 mol) of adipic acid are suspended in 150 ml of dimethylacetamide. 13.2 g of thionyl chloride are then added over the course of 10 minutes at approx. 50° C, whilst stirring, and the reaction mixture is stirred for a further 4 hours at 50° C.

Thereafter the yellowish solution obtained is allowed to run into approx. 1 liter of 2% strength hydrochloric acid. The amorphous precipitate solidifies to crystals after standing for several hours. After isolation and washing with water, N,N'-di-(3,5-di-t.butyl-4-hydroxyphenylpropionyl)-adipic acid dihydrazide is obtained in a yield of 55% (19 g). After recrystallisation from acetonitrile, the substance melts at 247° C.

What we claim is:

1. A process for the manufacture of 1,2-diacylhydrzaines of the formula Ia $$R_1-CO-NH-NH-CO-R_3 \qquad (Ia)$$

wherein $R_1$ and $R_3$ independently of one another are an aliphatic, cycloaliphatic, araliphatic, or aromatic radical, in which process 1 equivalent of an acyl hydrazide of the formula II $$R_1-CO-NH-NH_2 \qquad II$$

and approximately one equivalent of a carboxylic acid of the formula III

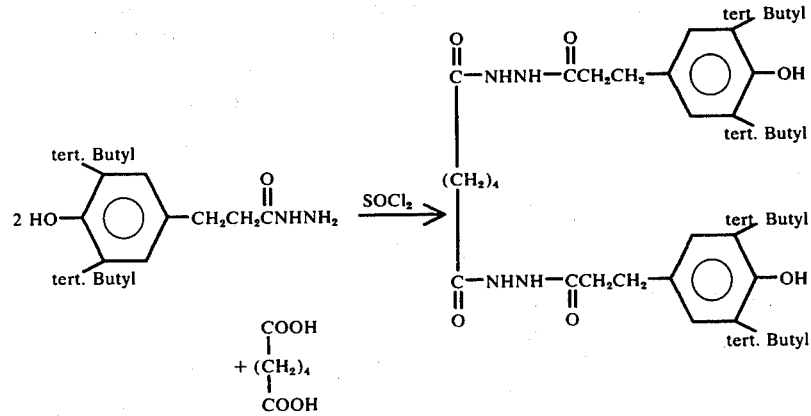

$R_3 - COOH$  (III)

are reacted with approximately one equivalent of thionyl chloride at a temperature of 50° to 180° C and in the presence of a catalyst selected from pyridine and dimethylformamide, provided that said catalyst may be omitted if the reaction is carried out in the solvent dimethylacetamide.

2. A process according to claim 1 for the manufacture of compounds of the formula Ia in which $R_1$ is unsubstituted phenyl, phenyl substituted by hydroxyl, unsubstituted aralkyl, aralkyl substituted by hydroxyl and/or lower alkyl, or alkyl, and $R_3$ is unsubstituted phenyl, phenyl substituted by hydroxyl or alkoxy, or alkyl 3. A process according to claim 2, wherein the reaction is carried out in an inert solvent.

4. A process according to claim 1, wherein the catalyst is pyridine.

5. A process according to claim 1, wherein the catalyst is dimethylformamide.

6. A process according to claim 1, wherein the reaction is carried out in chlorobenzene and the catalyst is pyridine or dimethylformamide.

7. Process according to claim 1 for the manufacture of

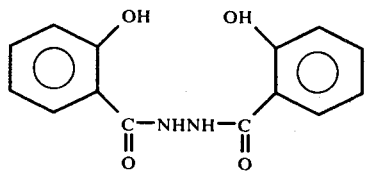

wherein one equivalent of

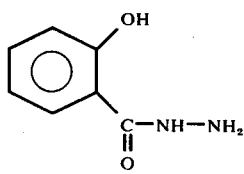

and approximately one equivalent of

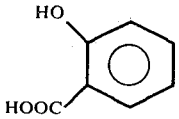

are reacted with approximately one equivalent of thionyl chloride, in chlorobenzene and in the presence of a catalyst selected from pyridine and dimethylformamide.

8. A process for the manufacture of 1,2-diacylhydrazines of the formula Ic $R_1-CO-NHNH-Y-NHNH-CO-R_1$  (Ic)

wherein $R_1$ is an aliphatic, cycloaliphatic, araliphatic, or aromatic radical, and Y is the diacyl radical of a divalent aliphatic, araliphatic, aromatic or heterocyclic dicarboxylic acid, in which process two equivalents of an acyl hydrazide of the formula II $R_1-CO-NH-NH_2$  (II)

and approximately one equivalent of a compound of the formula VI,'

$HO-Y-OH$  (VI)

are reacted with approximately two equivalents of thionyl chloride at a temperature of 50° to 180° C and in the presence of a catalyst selected from pyridine and dimethylformamide, provided that said catalyst may be omitted if the reaction is carried out in the solvent dimethylacetamide.

9. A process according to claim 8 for the manufacture of compounds of the formula Ic, in which $R_1$ is unsubstituted phenyl, phenyl substituted by hydroxyl, unsubstituted aralkyl, aralkyl substituted by hydroxyl and/or lower alkyl, or alkyl, and Y is a diacyl radical of a divalent alkanoic acid.

10. A process according to claim 8, wherein the reaction is carried out in an inert solvent.

11. A process according to claim 8, wherein the catalyst is pyridine.

12. A process according to claim 8, wherein the catalyst is dimethylformamide.

13. A process according to claim 8, wherein the reaction is carried out in chlorobenzene and the catalyst is pyridine or dimethylformamide.

* * * * *